United States Patent
Lerchenfeld et al.

(10) Patent No.: US 7,335,389 B2
(45) Date of Patent: Feb. 26, 2008

(54) BEVERAGES CONTAINING PLANT STEROLS

(75) Inventors: Erich P. Lerchenfeld, Altamonte Springs, FL (US); Donald E. Striegel, Clermont, FL (US)

(73) Assignee: The Coca-Cola Company, Atlanta, GA (US)

( * ) Notice: Subject to any disclaimer, the term of this patent is extended or adjusted under 35 U.S.C. 154(b) by 173 days.

(21) Appl. No.: 10/458,692

(22) Filed: Jun. 11, 2003

(65) Prior Publication Data

US 2003/0232118 A1    Dec. 18, 2003

Related U.S. Application Data

(60) Provisional application No. 60/387,574, filed on Jun. 12, 2002.

(51) Int. Cl.
   A23L 2/02        (2006.01)
(52) U.S. Cl. ...................................... 426/599; 426/590
(58) Field of Classification Search ................ None
   See application file for complete search history.

(56) References Cited

U.S. PATENT DOCUMENTS

| | | |
|---|---|---|
| 3,004,043 A | 10/1961 | Stern et al. |
| 3,085,939 A | 4/1963 | Wruble et al. ................ 167/65 |
| 3,881,005 A | 4/1975 | Thakkar et al. |
| 4,195,084 A | 3/1980 | Ong |
| 4,508,703 A | 4/1985 | Redziniak et al. |
| 5,043,329 A | 8/1991 | Lichtenberger |
| 5,244,887 A | 9/1993 | Straub |
| 5,496,813 A | 3/1996 | Eugster et al. |
| 5,880,300 A | 3/1999 | Kodali |
| 6,045,826 A | 4/2000 | Borowy-Borowski et al. |
| 6,054,144 A | 4/2000 | Burruano et al. |
| 6,063,776 A | 5/2000 | Ostlund, Jr. |
| 6,110,502 A | 8/2000 | Burruano et al. |
| 6,113,972 A | 9/2000 | Corliss et al. |
| 6,123,978 A | 9/2000 | Dartey et al. |
| 6,129,944 A | 10/2000 | Tiainen et al. |
| 6,190,720 B1 | 2/2001 | Yuan et al. |
| 6,191,172 B1 | 2/2001 | Borowy-Borowski et al. |
| 6,242,001 B1 | 6/2001 | Bruce et al. |
| 6,303,803 B1 | 10/2001 | Kodali |
| 6,387,411 B2 | 5/2002 | Bruce et al. |
| 6,391,370 B1 * | 5/2002 | Rogers et al. .............. 426/611 |
| 6,623,780 B1 | 9/2003 | Stevens et al. |
| 2002/0006461 A1 * | 1/2002 | Haarasilta et al. .......... 426/549 |
| 2002/0048606 A1 * | 4/2002 | Zawistowski ............... 424/489 |
| 2002/0064548 A1 * | 5/2002 | Yoon et al. ................. 424/439 |
| 2002/0192353 A1 * | 12/2002 | Cain et al. .................. 426/603 |
| 2003/0068425 A1 | 4/2003 | Khare |
| 2003/0129253 A1 * | 7/2003 | Milley et al. ............... 424/523 |
| 2003/0232796 A1 * | 12/2003 | Cooper et al. .............. 514/169 |
| 2004/0029844 A1 * | 2/2004 | Yoon et al. ................. 514/169 |
| 2004/0033202 A1 * | 2/2004 | Cooper et al. ................ 424/46 |
| 2004/0142087 A1 * | 7/2004 | Lerchenfeld et al. ........ 426/599 |
| 2005/0118203 A1 * | 6/2005 | Yoon et al. ................. 424/400 |
| 2005/0163872 A1 | 7/2005 | Khare |
| 2006/0034934 A1 | 2/2006 | DeGuise et al. |

FOREIGN PATENT DOCUMENTS

| | | |
|---|---|---|
| CA | 2310502 | 12/2000 |
| EP | 0897671 | 2/1999 |

(Continued)

OTHER PUBLICATIONS

Farquhar, John W., M.D., et al., *Circulation—Official Journal of the American Heart Association*, vol. XIV, pp. 77-82 (1956).

(Continued)

*Primary Examiner*—Carolyn Paden
(74) *Attorney, Agent, or Firm*—Finnegan, Henderson, Farabow, Garrett & Dunner, L.L.P.

(57) ABSTRACT

The invention relates to a process for producing a substantially stable dispersion without manufacturing aids, where the dispersion consists essentially of a hydrophobic plant sterol and an aqueous material, wherein the plant sterol is selected from plant sterols and plant stanols. The process comprises mixing the plant sterol with the aqueous material to form a first dispersion The next steps involve heating the first dispersion to form a heated mixture, followed by homogenizing the heated mixture to obtain a second dispersion of particles wherein the particle size of the hydrophobic plant sterol particles in the first dispersion and the second dispersion is from about 0.1 micron to about 30 microns. In one embodiment, the aqueous material consists essentially of a beverage concentrate, which includes a juice concentrate, such as a citrus juice concentrate, e.g., an orange juice concentrate. The invention also relates to a product produced by this process and a composition of matter which is a substantially stable dispersion of a hydrophobic plant sterol and an aqueous material wherein the plant sterol is selected from plant sterols and plant stanols, where in order to substantially avoid a powdery taste in the dispersion, the particle size of the plant sterol particles is from about 0.1 micron to about 30 microns and the majority of hydrophobic plant sterol particles within this range will be from about 0.2 microns to about 10 microns and will substantially follow a bell curve distribution. This composition may be made by the process of the invention, or may further include manufacturing aids selected from food grade emulsifiers, gums, starches and pectins.

63 Claims, 2 Drawing Sheets

FOREIGN PATENT DOCUMENTS

| | | |
|---|---|---|
| EP | 0947197 | 6/1999 |
| EP | 0985411 | 3/2000 |
| EP | 0986962 | 3/2000 |
| EP | 1005859 | 6/2000 |
| FI | 0098039 B | 12/1996 |
| FI | 0105887 B | 10/2000 |
| GB | 934686 | 8/1963 |
| GB | 1365661 | 9/1974 |
| WO | WO 94/27451 | 12/1994 |
| WO | WO 98/13023 | 4/1998 |
| WO | WO 98/58554 | 12/1998 |
| WO | WO 98/58629 | 12/1998 |
| WO | WO 99/15547 | 4/1999 |
| WO | WO 99/39715 | 8/1999 |
| WO | WO 99/44442 | 9/1999 |
| WO | WO 99/44642 | 9/1999 |
| WO | WO 99/53925 | 10/1999 |
| WO | WO 99/56729 | 11/1999 |
| WO | WO 99/63841 | 12/1999 |
| WO | WO 00/33669 | 6/2000 |
| WO | WO 00/41491 | 7/2000 |
| WO | WO 00/45648 | 8/2000 |
| WO | WO 00/45770 | 8/2000 |
| WO | WO 00/47213 | 8/2000 |
| WO | WO 00/50007 | 8/2000 |
| WO | WO 00/52029 | 9/2000 |
| WO | WO 00/69865 | 11/2000 |
| WO | WO 00/75165 | 12/2000 |
| WO | WO 00/78162 | 12/2000 |
| WO | WO 00/78789 | 12/2000 |
| WO | WO 01/00653 | 1/2001 |
| WO | WO 01/01960 | 1/2001 |
| WO | WO 01/28555 | 4/2001 |
| WO | WO 01/37681 | 5/2001 |
| WO | WO 01/37681 A1 | 5/2001 |
| WO | WO 2005/087200 A1 | 9/2005 |

OTHER PUBLICATIONS

*Hackh's Chemical Dictionary*, 3d Ed., pp. 392, 815-817 (1944).
*Hawley's Condensed Chemical Dictionary*, Twelfth Edition, p. 1100 (1993).
Kudchodkar, B.J., et al., *Atherosclerosis*, 23: 239-248 (1976).
McMurry, John, *Organic Chemistry*, Third Edition, pp. 916-950 (1992).
Pollak, O.J., *Circulation—Official Journal of the American Heart Association*, vol. VII, pp. 696-706 (1953).

\* cited by examiner

BEVERAGES CONTAINING PLANT STEROLS

RELATED APPLICATION

This application claims the benefit of priority from U.S. Provisional Application No. 60/387,574, filed Jun. 12, 2002, which is incorporated herein by reference.

BACKGROUND OF THE INVENTION

1. Field of the Invention

The invention relates to aqueous compositions, such as beverages, containing plant sterols for human and veterinary use and processes for their manufacture. Typical beverages include fruit and vegetable juices. Other typical beverages include sports beverages, drinks, or beverages employed to restore electrolytes lost due to illness. Further typical beverages include carbonated beverages including soft drinks and so-called "botanical flavor" drinks such as cola and other natural and artificial flavor drinks.

2. Related Art

Researchers have investigated methods of preventing atherosclerosis, one of the underlying causes of cardiovascular disease, and have evidence that cholesterol plays a role in this disease by contributing to the formation of atherosclerotic plaques in blood vessels, causing interference with blood circulation to the heart muscles, kidneys, brain and limbs. Some data show that a 1% reduction in a person's total serum cholesterol yields a 2% reduction in risk of coronary artery disease and a 10% decrease could prevent about 100,000 deaths in the United States annually. As early as 1953, the scientific literature reported that plant sterols have some effect in reducing atherosclerotic events in mammals, reduction in blood serum cholesterol in man and the reduction of serum cholesterol in young men with atherosclerotic heart disease. (Pollak, Circulation 7,696-701; 702-706 (1953); Farquhar et al., Circulation, 14, 77-82 (1956)). Other scientific literature establishes that plant sterols and stanols do, in fact, lower the level of serum cholesterol in humans, however, because of poor solubility in water, it was difficult to prepare products suitable for human and veterinary consumption that contained these plant sterols or stanols.

For the most part, they were employed in margarines and other so-called spreads or similar food products because of their hydrophobic properties. U.S. Pat. Nos. 3,881,005 and 4,195,084, both assigned to Eli Lilly, describe grinding or milling plant sterols in order to enhance their solubility. Eli Lilly at one time marketed a sterol preparation from tall oil and later from soybean oil under the trademark Cytellin that lowered serum cholesterol by about 9%. Kuccodkar et al., Atherosclerosis, 23: 239-248 (1976). The product, however, never received widespread consumer acceptance.

Fruit juice-containing products, i.e., aqueous-based beverages and preparations containing fruit juice (as well as concentrates for preparing such beverages and products) are used in the art, and have achieved a relatively high degree of commercial acceptance. The incorporation of hydrophobic ingredients into these products presents a difficulty well known in the art since hydrophobic ingredients have a different density than water and as a result, at the time of purchase and consumption of the product, a hydrophobic component may separate and float to the surface or sink to the bottom. The hydrophobic component that floats to the surface produces undesirable "ringing," which is found in beverages, such as juices containing a hydrophobic ingredient with a density less than water, and results in a product that is non-uniform throughout the container.

Fruit juice-containing products packaged in transparent or translucent (e.g., glass or plastic) containers must avoid this separation since aesthetically undesirable visible separation of the product impacts on consumer acceptance. Agitation of the fruit juice-containing product in its container prior to use provides a temporary dispersion of the hydrophobic ingredient, however, this only amounts to a short term solution, as the hydrophobic ingredient can separate again following agitation. Hydrophobic, fat-soluble or oleophilic ingredients, including vitamins, oils, extracts, flavors, and sterols, when added to fruit juice-containing products require special treatment to ensure incorporation either by suspension or dispersion into the fruit juice-containing product so that they will not separate.

Prior art attempts to overcome these difficulties typically make use of several methods including homogenization, encapsulation, and/or the addition of stabilizers, gums, emulsifiers, and the like, however, these methods increase the cost of the product, and in some instances are illegal in certain standardized products such as, a citrus juice, e.g., orange juice. The consumer may also find some of these products undesirable from a labeling, texture, and viscosity standpoint. Stabilizers and gums often add viscosity, i.e., thickness to a fruit juice-containing product thereby detracting from its organoleptic impression. Additionally, dispersing plant sterols in juices or drinks causes the beverage to have a powdery texture, which also impacts negatively on consumer acceptance Because of consumer recognition and acceptance, some juice beverages should maintain a turbid appearance and should not produce a ring at the surface of the juice when in the container or a glass, making it necessary to provide a fruit juice and/or fruit juice concentrate containing hydrophobic materials in a stable dispersion. Consumer recognition and acceptance of turbidity in some fruit juice products such as citrus juices, e.g., orange juice and other beverage products, requires stability of the product for this reason, both during refrigeration or the shelf life of the product, as well as at the point of consumption.

Tiainen et al., U.S. Pat. No. 6,129,944 describes a method for producing a product containing a plant sterol by forming a homogeneous suspension of a microcrystalline plant sterol and a sweetening agent in an aqueous solution.

Vulfson et al., WO 00/41491 discloses hydrophobic compounds such as plant sterols and lycopenes as supplements to food products and beverages such as oleomargarine products, drinks, soups, sauces, dips, salad dressings, mayonnaise, confectionery products, breads, cakes, biscuits, breakfast cereals and yogurt type products. Vulson et al., in combining the plant sterol or lycopene with the food product, theorizes that the food product which has both hydroxyl and carboxyl groups interacts with the surface of the sterol or lycopene.

The reference goes on to describe producing a fine suspension of plant sterols in water in the absence of surfactants and without grinding the plant sterol with sugars as disclosed U.S. Pat. Nos. 3,085,939; 4,195,084; 3,881,005 and GB 934,686. Vulfson et al. by contrast, forms a suspension or slurry of plant sterols in water at from about 10% to about 30% (by weight) of sterol by extensive homogenization using conventional methods and a small volume of a concentrated aqueous solution of the food product, which the inventors describe as a "coating material."

Haarasilta et al., WO 98/58554, describes a premix used in the food industry containing a pulverized plant sterol and a conventional foodstuff ingredient such as fruit, vegetable or berry type of material, particularly in a powder form and methods for preparing the premix. Grinding the plant sterol and the foodstuff such as berries, fruits, or vegetables according to methods and devices disclosed in Finnish patent applications FI 963 904 and FI 932 853 and with a grinder operating on the so-called impact milling principle, such as an Atrex mill manufactured by Megatrex Oy, produce this result. The inventors note that when applying the process of the invention to cereal in combination with a plant sterol, the temperature of the cereal grains rises due to the effect of mechanical energy on the grains, thereby providing heat treatment of the grains in conjunction with grinding.

Zawistowski, WO 00/45648, describes a method of preparing microparticles of plant sterols and plant stanols or mixtures of both by dispersing and suspending the plant sterols and plant stanols in a semi-fluid, fluid or viscous vehicle and exposing the vehicle so formed to impact forces. The method involves dispersing or otherwise suspending the plant sterol and/or plant stanol in a suitable semi-fluid, fluid or viscous vehicle followed by applying impact forces to the vehicle to produce microparticles. Zawistowski develops these impact forces by creating high-shear either with an air-atomization nozzle, a pneumatic nozzle, a high-shear mixer, or colloid mill, but preferably a microfluidizer commercially available from Microfluidics Incorporation, Newton, Mass.

Zawistowski observed that the plant sterols and/or plant stanols prepared in this way have greater "solubility" not only in oil based delivery systems but also in other media and can be incorporated into beverages such as colas, juices or dietary supplement and/or milk replacement drinks. (p. 8).

Gottemoller, WO 01/37681 A1, also describes a process of combining a plant sterol and/or plant stanol with a water-soluble protein and optionally an emulsifier by grinding the plant sterols and plant stanols or milling it to produce a powdered product before adding it to an aqueous material.

Tarr et al., WO 94/27451, describes a process for making a thickener from citrus fruit for beverages by preparing a slurry of water and citrus pulp having a solids content of from 0.15% to 10% by weight (anhydrous) followed by heating the slurry to a temperature from 70° C. to 180° C. (158° F. to 356° F.) for 2 to 240 minutes, and subjecting the slurry to high shear treatment at a shear rate of from 20,000 $sec^{-1}$ to 100,000,000 $sec^{-1}$ by homogenization at a pressure of from 1,000 psig to 15,000 psig and colloidal milling.

It would be an advantage to overcome at least one of the difficulties in the related art. At least one of these other advantages are realized according to the present invention which provides a process for producing a substantially stable dispersion consisting essentially of a hydrophobic plant sterol and an aqueous material such as an aqueous beverage concentrate, and products made by this process, all of which substantially obviate one or more of the limitations or disadvantages of the processes and compositions of the related art without increasing viscosity, imparting off-flavors, or a powder taste, introducing undesirable ingredients, or producing an undesirable visual appearance.

The specification sets out additional features and advantages which may be realized by the invention, which in part, a skilled artisan will find apparent from the description and may learn by practice of the invention, and who will realize the objectives and other advantages of the invention obtained by the process and composition particularly pointed out in the written descriptions and claims hereof.

SUMMARY OF THE INVENTION

To achieve at least one of these or other advantages and in accordance with the purpose of the invention, as embodied and broadly described, the inventors have found a process for producing a substantially stable dispersion consisting essentially of a hydrophobic plant sterol and an aqueous material, for example, an aqueous beverage concentrate, for example a juice concentrate, wherein the plant sterol is selected from plant sterols and plant stanols. Unless otherwise indicated, the term "plant sterol," as used in this specification and the claims, is intended to include both a plant sterol and a plant stanol. The process comprises mixing the hydrophobic plant sterol with the aqueous material to form a first dispersion of particles of the hydrophobic plant sterol and the aqueous material in which the particle size of the hydrophobic plant sterol particles in the first dispersion is from about 0.1 microns to about 50 microns. The process then provides for heating the first dispersion of particles of the hydrophobic plant sterol and the aqueous material to a temperature of from about 43° C. to about 100° C. (about 110° F. to about 212° F.) for a period of time of from about 1 second to about 20 seconds to form a heated first dispersion followed by homogenizing the heated first dispersion to obtain a second dispersion of particles of the hydrophobic plant sterol and the aqueous material, wherein the particle size of the hydrophobic plant sterol particles in the second dispersion is from about 0.1 microns to about 50 microns. The process of the invention and resultant composition do not require the use of gums and/or emulsifiers in order to obtain a stable dispersion of the plant sterols in the aqueous material without separation, flavor impact and texture impact, especially in the manufacture of juice concentrates, such as citrus juice concentrates, e.g., orange juice concentrates.

A substantially stable dispersion according to the invention comprises a dispersion of a hydrophobic plant sterol in an aqueous material produced according to the process of the invention that results in a dispersion where the plant sterol does not separate from it over a period of time up to about 12 months, after subjecting the dispersion to several heating and cooling cycles and/or shelf storage during this time. When employed in citrus juice concentrates, if the plant sterol settles, it settles with the sinking pulp, which is a natural occurrence for citrus juices.

Citrus beverages such as orange juice have two types of pulp, one floats and the other sinks. Pulp that gives orange juice its cloud comprises a sinking pulp whereas floating pulp rises to the surface of the juice and the container. Plant sterols have a density lower than water and as a result will float to the top of an aqueous beverage such as a citrus beverage concentrate or juice. If not properly dispersed, the plant sterol will form a white ring at the top of the citrus beverage. One of the advantages of the present invention comprises providing a substantially stable dispersion of the plant sterol and aqueous material such as a citrus beverage concentrate or citrus beverage, with no separation of the plant sterol in a manner to form white rings at the top of the beverage. The inventors have found that the plant sterols of the present invention, which comprises the plant sterol in combination with at least one fruit juice concentrate, citrus juice concentrate or beverage such as orange juice, may not rise to the surface of the beverage, but rather may remain dispersed in the beverage and causes an increase in the volume of sinking pulp at the bottom of the beverage. The increased volume of sinking pulp suggests the presence of the plant sterol in the sinking pulp. In any event, according to the invention, the fruit juice, citrus beverage concentrate, or citrus beverage formulated according to the present invention may be substantially free if not totally free of plant sterols that float to the surface.

In another aspect, forming the dispersion of the invention includes cooling the heated first dispersion to a temperature of from about 22° C. (about 72° F.) up to about 71° C. (about 160° F.) for a period of time of from about 1 second to about 12 seconds prior to homogenizing. The process also involves conducting the homogenizing at different pressures and multiple steps, and optionally at different temperatures of from about 22° C. (about 72° F.) up to about 71° C. (about 160° F.).

In a further embodiment of the invention, the aqueous material may comprise an aqueous beverage concentrate such as a fruit juice concentrate, e.g., a citrus juice concentrate such as an orange juice concentrate. The invention also includes a composition of matter comprising the aqueous beverage concentrate in combination with a plant sterol, an aqueous beverage concentrate in combination with a plant sterol and diluted with water or other aqueous composition, or a product made by the process described in the written description.

Another aspect of the invention relates to the discovery that the process of the invention for manufacturing the composition to avoid separation of the plant sterol requires either the use of a beverage concentrate, or beverage, or aqueous medium having a viscosity of from about 100 cps to about 30,000 cps, or from about 5,000 cps to about 30,000 cps, or from about 6,000 cps to about 18,000 cps. Where the beverage concentrate, or beverage, or aqueous medium does not fall within these viscosity ranges, the composition of the invention may be made using the process steps employed in the invention to form a first dispersion and a second dispersion, or any other process, but with the use of manufacturing aids used in the art to bring the viscosity into these ranges.

The invention also relates to the discovery that a dispersion of a hydrophobic plant sterol in an aqueous material avoids the prior art difficulty of imparting a powdery taste to the dispersion, when the particle size of the hydrophobic plant sterol particles is from about 0.1 micron to about 50 microns, or the majority of hydrophobic plant sterol particles within this range will be from about 0.2 microns to about 10 microns, or in any event will substantially follow a bell curve distribution, for any of these particle size distributions. Although the process of the invention can be used to obtain this composition, this aspect of the invention relates to a composition having this particle size range, irrespective of the process used to manufacture the composition. In this aspect of the invention, the composition may optionally contain so-called manufacturing aids, used in the art. The term "majority" as used in this specification and the claims means greater than 50%.

DETAILED DESCRIPTION

Figure 1:
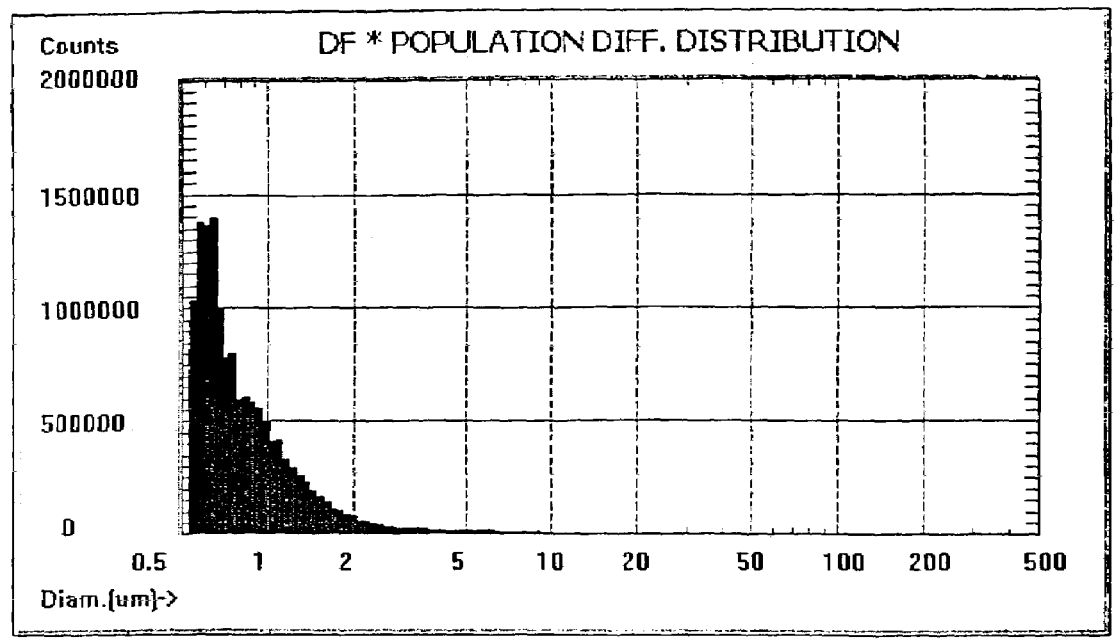
FIG. 1 is an example of the particle size distribution of a sample of micronized plant sterol having a total plant sterol content of greater than about 93%, and composed of β-sitosterol, β-sitostanol, campesterol, campestanol, stigmasterol, spinosterol, avenasterol, and brassicasterol, the mixture having a melting point of about 138° C. to about 141° C., derived from vegetable oils and tall oils, and supplied by MB Multi Bene Health Oy Ltd. of Finland.

Accordingly, the invention relates to a process for producing a substantially stable dispersion comprising at least one hydrophobic plant sterol and an aqueous material such as an aqueous beverage concentrate wherein the at least one plant sterol is selected from plant sterols and plant stanols, and wherein the dispersion does not contain any added emulsifiers and thickening agents and other so-called "manufacturing aids," used in the food arts, e.g., encapsulation materials.

Another aspect of the invention relates to the discovery that the process of the invention for manufacturing the composition to avoid separation of the plant sterol requires either the use of a beverage concentrate, or beverage, or aqueous medium having a viscosity of from about 100 cps to about 30,000 cps, or about 5,000 cps to about 30,000 cps, or from about 6,000 cps to about 18,000 cps, or from about 8,000 cps to about 15,000 cps. The viscosity measurements referred to herein were determined using a Brookfield Viscometer Model # LVDV-11+, using Spindle #3 at a speed of 20 rpm. Again, where the beverage concentrate, or beverage, or aqueous medium does not fall within these viscosity ranges, the composition of the invention may be made using the process steps employed in the invention to form a first dispersion and a second dispersion, or any other process used in the food arts, but with the use of manufacturing aids used in the food arts to bring the viscosity into these ranges. These manufacturing aids may be added to the composition prior to beginning the process, or at any stage during the process.

In mixing the hydrophobic plant sterol with the aqueous material such as an aqueous beverage concentrate to form a first dispersion and/or a second dispersion of particles of the hydrophobic plant sterol and the aqueous material, the particle size of the hydrophobic plant sterol particles in the first dispersion and/or the second dispersion is from about 0.1 microns to about 100 microns, or about 0.1 microns to about 50 microns, or from about 0.1 microns to about 30 microns, or from about 0.1 micron to about 10 microns, and in one embodiment will substantially follow a bell curve distribution. In another embodiment, in order to substantially avoid a powdery taste in the aqueous material, or concentrate, or beverage, the particle size of the hydrophobic plant sterol particles in the first dispersion and/or the second dispersion is from about 0.1 micron to about 30 microns, or where the majority of particles will range in size in any one of the foregoing ranges of from about 0.2 microns to about 10 microns, or about 0.2 microns to about 2.5 microns, or about 0.4 microns to about 1.5 microns, or about 0.3 microns to about 0.4 microns, and in a further embodiment will substantially follow a bell curve distribution. All of the foregoing particle sizes and particle size ranges may also vary from plus or minus about 30%, or plus or minus about 20%, or plus or minus about 10%. Hydrophobic plant sterol particles of all of the above mentioned sizes and size ranges are well known in the art and may be obtained through commercial suppliers such as Cargill Co.

One aspect of the invention therefore comprises a process for producing a substantially stable dispersion consisting essentially of a hydrophobic plant sterol and an aqueous material, wherein said plant sterol is selected from plant sterols and plant stanols comprising:

(a) mixing said hydrophobic plant sterol with said aqueous material to form a first dispersion of particles of said hydrophobic plant sterol and said aqueous material;

(b) heating said first dispersion of particles of said hydrophobic plant sterol and said aqueous material to form a heated mixture;

(c) homogenizing said heated mixture to obtain a second dispersion of particles of said hydrophobic plant sterol and said aqueous material, wherein the particle size of said hydrophobic plant sterol particles in said first dispersion is from about 0.1 microns to about 30 microns, or the particle size of said hydrophobic plant sterol particles in said second dispersion is from about 0.1 microns to about 30 microns, or wherein the particle size of said hydrophobic plant sterol particles in both said first dispersion and said second dispersion is from about 0.1 microns to about 30 microns.

Another aspect of the invention relates to a composition of matter which is a substantially stable dispersion of a hydrophobic plant sterol or plant stanol and an aqueous material which, in order to substantially avoid a powdery taste in the aqueous material, or concentrate, or beverage comprises hydrophobic plant sterol or plant stanol particles as described above. The composition of matter having this particle size, or particle size and particle size distribution to substantially avoid a powdery taste in the aqueous material, or concentrate, or beverage product may be made according to the process of the invention, or by any other process used in the food arts, so long as it contains the plant sterol or plant stanol that has the particle size, or particle size and particle size distribution that avoids the powdery taste in the finished product, and, when not manufactured according to the process of the invention, may optionally contain manufacturing aids used in the food arts. These manufacturing aids may be used in amounts of from about 0.001% by wt. to about 50% by weight of the plant sterol, or from about 0.01% by wt. to about 30% by weight of the plant sterol, or from about 0.01% by wt. to about 25% by weight of the plant sterol or plant stanol, or from about 0.1% by wt. to about 20% by weight of the plant sterol or plant stanol, all based on the aqueous material, or concentrate, or beverage product.

The so-called "manufacturing aids" include encapsulation aids, starches, and gums used as thickening agents employed in the food arts, and pectin, de-methylated pectin and other pectin derivatives used in the food arts. The emulsifiers comprise modified food starches and other similar food-type emulsifiers whereas the gums include gum Arabic, seaweed extracts, alginates, plant or seed gums such as guar gum or animal derived products such as gelatin as well as xanthan gum, locust gum, carrageenan and the like. In addition to gum Arabic, other water soluble gums employed comprise angico gum, cebil gum, mesquite gum, cedar gum, and Indian gum, whereas the gums slightly soluble in water include tragacanth, sterculia, hog gum, amrad gum, and satinwood gum or gums that swell in water such as cherry gum, Sonora gum or sassa gum. Other gums included in this aspect of the invention are defined in Hackh's Chemical Dictionary, 3d Ed., p. 392.

The invention also relates to compositions as set forth herein as well products produced by the process of the invention.

Scientific literature describes at least 44 plant sterols, and the skilled artisan can select any plant sterol from those that are available when practicing the present invention. The present invention, also involves using some of the plant sterols employed in the art. Some plant sterols in this regard include sitosterol, campesterol, stigmasterol, spinosterol, taraxasterol, brassicasterol, desmosterol, chalinosterol, poriferasterol, clionasterol, and ergosterol. The invention also employs mixtures of plant sterols, such as two component, three component, and four component mixtures.

The source of these and other plant sterols are rice bran, corn bran, corn germ, wheat germ oil, corn oil, safflower oil, oat oil, olive oil, cotton seed oil, soybean oil, peanut oil, black tea, green tea, colocsia, kale, broccoli, sesame seeds, shea oils, grapeseed oil, rapeseed oil, linseed oil, canola oil, tall oil and other oils obtained from wood pulp.

Plant sterols may also be hydrogenated to produce plant stanols. Accordingly, the plant stanols of the present invention are described as the hydrogenation products of the various plant sterols such as sitosterol but may also be obtained naturally from various plants used in the art, without hydrogenating the plant sterol. Thus, the term "hydrogenation product of plant sterols" as applied to plant stanols, and as used herein, includes not only the synthetic plant stanols but also those obtained from natural sources. Some plant stanols in this regard include sitostanol, campestanol, stigmastanol, spinostanol, taraxastanol, brassicastanol, desmostanol, chalinostanol, poriferastanol, clionastanol, and ergostanol. The skilled artisan can also select any plant stanol from those that are available. The invention also employs mixtures of plant stanols, such as two component, three component, and four component mixtures, as well as mixtures of plant sterols and plant stanols such as two component, three component, and four component mixtures.

Both the plant sterols and plant stanols include the various position isomers and stereo isomeric forms used in the art, such as the $\alpha$ and $\beta$ isomers as well as plant sterols and plant stanols that contain small (from one to about four carbon atom) side chains. $\alpha$-sitosterol and $\beta$-sitostanol respectively comprise one of the most effective plant sterols and one of the most effective plant stanols for lowering serum cholesterol in mammals.

The mixing of the hydrophobic plant sterol with the aqueous beverage concentrate to form a first dispersion of particles is conducted at temperatures from about $-10°$ C. to about $100°$ C. (about $14°$ F. to about $212°$ F.), or from about $0°$ C. to about $82°$ C. (about $32°$ F. to about $180°$ F.), or about $17°$ C. to about $64°$ C. (about $64°$ F. to about $148°$ F.), or about $24°$ C. to about $57°$ C. (about $75°$ F. to about $135°$ F.) for a period of time of from about 0.1 minutes to about 120 minutes, or from about 5 minutes to about 60 minutes, or from about 15 minutes to about 30 minutes, to form a first dispersion.

The apparatus employed for making the first dispersion of particles of the at least one hydrophobic plant sterol and aqueous material, such as a beverage concentrate comprises a high shear mixer (such as Arde-Barinco Model #CJ-4) or any large capacity (e.g., about 50 to about 300 gal.) high shear mixer. A commercial device for making the first dispersion comprises a "Liquiverter" (Trademark) manufactured under the trade name APV Liquiverter model 200 CLV, manufactured by APV, an Invensys Company.

Figure 2:
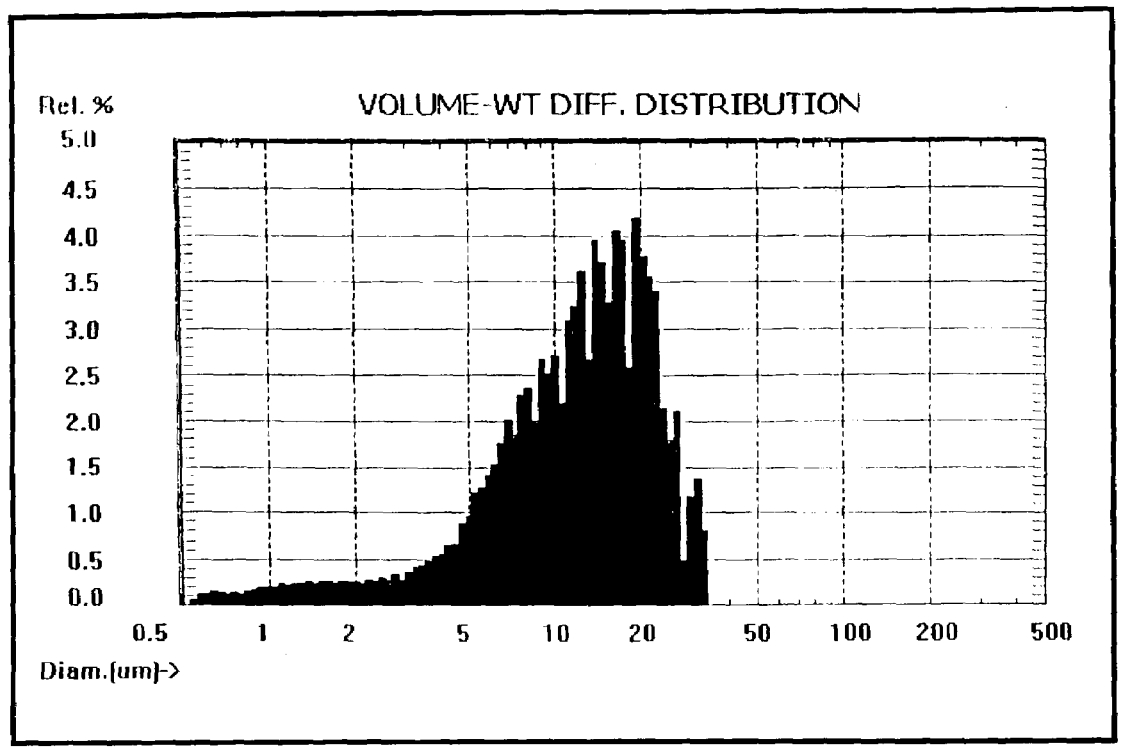
FIG. 2 shows the volume distribution of the micronized plant sterol of FIG. 1.

In one embodiment, the plant sterols supplied may be micronized to a size of about 0.5 to about 10 microns. FIG. 1 shows an exemplary particle size distribution of the micronized plant sterol before heating according to one embodiment of the present invention. In FIG. 1, "DF* Population Diff. Distribution" refers to the dilution factor multiplied by Population Differential Distribution, i.e., the number of counts in each channel had been multiplied by the factor that the sample was diluted, to yield the number of counts in the neat sample. FIG. 2 shows an exemplary volume distribution of the micronized plant sterol before heating according to one embodiment of the present invention. In FIG. 2, "Volume-Wt-Diff. Distribution" refers to Volume Weighted Differential Distribution, i.e., taking all of the particles and looking at their volumes and making a determination of the contribution of each size channel to the overall volume of the sample. U.S. Pat. No. 6,129,944 describes the method and apparatus used to manufacture the plant sterol composition of FIGS. 1 and 2; however, the food industry also employs spray-drying techniques to form these compositions.

In FIG. 1, the numerical values for each of the reported "counts" (the values in the ordinate) and the numerical values for each of the reported particle diameters in microns (the values in the abscissa) can vary anywhere from plus or minus about 30% or plus or minus about 20% or plus or minus about 10% whereas in FIG. 2, the numerical values for each of the reported relative percentages (the values in the ordinate) and the numerical values for each of the reported particle diameters in microns (the values in the abscissa) can vary anywhere from plus or minus about 30% or plus or minus about 20% or plus or minus about 10%. Although the data of FIG. 1 and FIG. 2 refer to a specific plant sterol product, these data may also define the particle size and particle size distribution of any one of the plant sterols employed according to the invention, such as those described in this specification, and those that are used in the art.

It is believed that in forming the first dispersion of a hydrophobic plant sterol and aqueous material the shear stress and/or shear rate applied to the hydrophobic plant sterol with the aqueous medium is sufficient to form a somewhat stable dispersion of particles of the hydrophobic plant sterol and the aqueous material, however, the first dispersion does not have sufficient long term stability that would allow its use in consumer products such as juices, beverages, juice drinks and the like. Because the plant sterol has a relatively high melting point (anywhere from about 212° F. (about 100° C.) to about 400° F., (about 204° C.)) any agitation applied to it at lower temperatures does not tend to allow the mixing process to reduce enough of the hydrophobic plant sterol to a small particle size, which has greater long-term suspension retaining properties. It is therefore believed that heating the first dispersion of particles to form a heated mixture, followed by homogenizing the heated mixture to form a second dispersion avoids the foregoing disadvantages.

The particle size of the hydrophobic plant sterol of both the first dispersion and the second dispersion substantially follows a bell curve particle size distribution well known to a person with ordinary skill in the art.

The aqueous material can comprise water, and water with additional compounds, and compositions dissolved or dispersed in it, either as a dispersion of solids in water or an emulsion of a liquid in water or water in a liquid. This defines the aqueous material of the invention, prior to mixing it with the hydrophobic plant sterol. When employing the aqueous material with a dissolved or dispersed compound or composition, the solids content of the aqueous material, such as an aqueous beverage concentrate is from about 200 grams per liter of the aqueous beverage concentrate to about 1000 grams per liter of the aqueous beverage concentrate, or about 400 grams per liter to about 900 grams per liter, or about 600 grams per liter to about 800 grams per liter. "Solids content," as that term applies to the "aqueous material" of the present invention, also includes any liquid added to the water used in forming an emulsion type of "aqueous material" as defined herein.

The hydrophobic plant sterol is present in the first dispersion and/or the second dispersion in an amount from about 1 gram to about 100 grams of oleophilic plant sterol per liter or from about 10 grams to about 60 grams per liter, or about 20 grams to about 30 grams per liter of the aqueous material, or concentrate, or beverage product. In one embodiment, the hydrophobic plant sterol is present in the first dispersion and/or the second dispersion in an amount from about 15 grams to about 30 grams of hydrophobic plant sterol to about one liter of the aqueous material, or concentrate, or beverage product.

In another aspect of the invention, the heated first dispersion is cooled to a temperature from about 0° C. to about 100° C. (about 32° F. to about 212° F.), or about 13° C. to about 87° C. (about 55° F. to about 189° F.), or about 26° C. to about 75° C. (about 78° F. to about 167° F.) for a period of time from about 1 second to about 30 seconds, or from about 2 seconds to about 10 seconds, or from about 5 seconds to about 7 seconds prior to homogenizing to form the second dispersion of particles of the hydrophobic plant sterol and the aqueous material.

In a further embodiment, the heated first dispersion is cooled to a temperature of from about 22° C. (about 72° F.) to about 71° C. (about 160° F.) for a period of time of from about 1 second to about 12 seconds prior to the homogenizing.

The homogenizing of the heated mixture to obtain a second dispersion of particles of the at least one hydrophobic plant sterol and the aqueous beverage concentrate is conducted in a homogenizer (such as APV model #APV 1000), which may function by forcing the dispersion through a small orifice at high pressures. The homogenizing may be carried out at a pressure from about 100 psi to about 14,500 psi, or 500 psi to about 10,000 psi, or 1000 psi to about 5000 psi. In one embodiment, the homogenizing is carried out at a pressure of about 2000 psi to about 5000 psi.

The invention also relates to conducting homogenizing at different pressures in single or multiple stages such as one stage, two stages, three stages, four stages or more.

Homogenization at high pressures and low pressures can proceed according to any of the following parameters and combinations thereof:

| High Pressure | Low Pressure |
|---|---|
| about 3000 psi | about 400 psi |
| about 3000 psi | about 500 psi |
| about 5000 psi | about 1000 psi |
| about 3400 psi | about 600 psi |

The sequence generally is to conduct the homogenization first at a high pressure than a low pressure, but the method of the invention also includes conducting the homogenization with different sequences of pressures, and in one embodiment, with more than one homogenizer.

Various beverage concentrates can be employed as the aqueous material according to the method of the invention, however, in one embodiment, the process involves producing a substantially stable dispersion comprising at least one hydrophobic plant sterol and an aqueous citrus juice concentrate such as an orange juice concentrate.

In its broader aspect, the aqueous material of the invention comprises water, and water in combination with nutrients, flavorants, sweeteners, carbon dioxide and other gases, and combinations thereof. In another aspect the aqueous material is a concentrate of a fruit juice, or fruit flavor, such as citrus juices including orange, lemon, lime, tangerine, mandarin and, grapefruit juice, and other juice and fruit flavor concentrates such as acerola, grape, pear, passion fruit, pineapple, banana, apple, cranberry, cherry, raspberry, peach, plum, grape, currant, cranberry, blackberry, blueberry, strawberry, mirabelle, watermelon, honeydew, cantaloupe, mango, papaya, botanical flavors such as flavors derived from cola, tea, coffee, chocolate, vanilla, almond, vegetable juices and flavors such as tomato, cabbage, celery, cucumber, spinach, carrot, lettuce, watercress, dandelion, rhubarb, beet, cocona, guava, han guo, and mixtures thereof, such as two component, three component and four component mixtures.

The aqueous material of the invention also includes concentrates of typical sport beverages, and beverages used to treat loss of fluids due to illness, and which contain sucrose syrup, glucose-fructose syrup, citric acid, sodium citrate, monopotassium phosphate and potassium salts, and other materials for replenishing lost electrolytes, whether as a product requiring the addition of water or in admixture with water.

The concentrates can be diluted with water to form juices or drinks, and where the concentrate includes a sugar or mixture of sugars, it can be diluted with water to about 2° Brix to about 20° Brix, or about 6° Brix to about 16° Brix, or about 10° Brix to about 12° Brix. The sugars employed according to the present invention generally comprise carbohydrate materials such as fructose, sucrose, glucose and the like as well as the other sugars used in the art as described by McMurry, *Organic Chemistry*, Third Edition, pp. 916-950, *Hawley's Condensed Chemical Dictionary*, Twelfth Edition, p. 1100, and *Hackh's Chemical Dictionary*, Third Edition, pp. 815-817. Mixtures of sugars can also be used, such as the two component, three component and four component mixtures.

The process for producing a substantially stable dispersion consisting essentially of a hydrophobic plant sterol and an aqueous material as well as the product produced by this process according to the present invention may also have water soluble vitamins, such as vitamin C, vitamin B6 and/or vitamin B12, folic acid, or oil soluble vitamins such as vitamin A, beta carotene, vitamin B, e.g., the D vitamins, vitamin E, and vitamin K added thereto and any mixtures thereof, such as the two component, three component and four component mixtures, either before, during or after the production of the substantially stable dispersion of the invention, e.g., by adding the vitamin or vitamins to the step for manufacturing the first dispersion or the step for manufacturing the second dispersion, or both such steps. The addition of a vitamin, such as vitamins B and E varies to obtain an RDA from about 1% to about 100%, or about 5 to about 30%, or about 15 to about 20% of the RDA for each vitamin per unit serving.

The following example illustrates the invention.

Combining the following components provided a base mixture of hydrophobic plant sterol with an aqueous material before subsequent processing to form a first dispersion. The composition was formulated to obtain the following:

| Base Ingredients | |
|---|---|
| Desired Volume | 0.75 Gallons |
| Water | 180.2 grams |
| Orange Concentrate | 3363.0 grams1 |
| Orange Flavor | 53.1 grams |
| Orange Oil | 2.7 grams |
| Plant sterol | 76.7 grams2 |
| Total | 3675.5 grams |

1Refractometer ° Brix, 65 (corrected for acid); acid, 3.71% (wt./wt.).
2ADM 09/2001 consisting essentially of betasitosterol, betasitostanol, campesterol, campestanol, stigmasterol, spinosterol, avenasterol, or brassicasterol having a particle size of from about 0.5 microns to about 30 microns.

Finished Product Ingredients

| | |
|---|---|
| Desired Volume | 4.8 gallons |
| Water | 4.05 gallons |
| Base | 0.75 gallons |

| Base Specifications | OPT. | MIN. | MAX. |
|---|---|---|---|
| Percent Soluble Solids | 61.56 | 61.14 | 62.39 |
| Refractometer ° Brix | 61.15 | 60.74 | 61.99 |
| % Acid w/w as citric | 3.42 | 3.12 | 3.72 |
| ° Brix/acid ratio | 18.0 | 16.4 | 20.0 |

The substantially stable dispersion of the oleophilic plant sterol and the orange juice concentrate as the aqueous material had a concentration of 61.15° Brix (refractometer Brix, corrected for acid).

The mixture was stirred using an Arde-Barinco Model No. CJ-4 high shear mixer at 7000 rpm for about 15 minutes and heated to 82.2° C. (180° F.) in 8 seconds and chilled to about 43.3° C. to about 60° C. (about 110° F. to about 140° F.) in about 5 seconds to produce a first dispersion having an average particle size of about 10 microns and a particle size distribution of about 0.5 microns to about 30 microns with the maximum particle size being about 30 microns.

Homogenizing the first dispersion in an APV homogenizer, Model No. APV 1000 from the APV Homogeniser Group (An Invensys Company) at 60° C. (140° F.) at 3400 psi and then 600 psi produced the second dispersion.

The second dispersion comprised a substantially stable dispersion consisting essentially of the hydrophobic plant sterol and the orange juice concentrate as the aqueous material. Adding water to the substantially stable dispersion produced an orange juice product of 12.00° Brix. The product is manufactured to the following specifications:

| Product Specifications | OPT. | MIN. | MAX. |
|---|---|---|---|
| Percent Soluble Solids | 12.00 | 11.90 | 12.20 |
| Refractometer ° Brix | 11.92 | 11.82 | 12.12 |
| % Acid w/w as citric | 0.67 | 0.65 | 0.69 |
| ° Brix/acid ratio | 18.0 | 17.3 | 18.8 |

The various numerical ranges describing the invention as set forth throughout the specification also include any combination of the lower ends of the ranges with higher ends of the ranges set forth herein, and any single experimental numerical value and other single numerical value set forth herein that will increase or reduce the scope of the lower limits of the range, or the scope of the higher limits of the range, where the range includes, inter alia, ranges of time, temperature, pressure, concentrations of compounds and compositions, including °Brix, ratios of these compounds and compositions to one another, particle size, particle size distribution, percentage variations, and the like, as well as all whole number and/or fractional number values encompassed by these ranges, and ranges encompassed within these ranges. The term "about" as it applies to individual numerical values, and numerical values stated in the ranges of the present specification means slight variations in these values. For example, as is well known in the art, concentration values given in °Brix may vary ±2%, time values given in seconds may vary ±1 second, time values given in minutes may vary ±1 minute, temperature values given in °C. or °F. may vary ±2%, pressure values given in psi may vary ±10%, particle size values given in microns may vary ±5%, solids content given in g/L may vary ±2%, and viscosity values given in cps may vary ±10%. The terms "substantial" and "substantially" as used in the specification mean either that which is entirely specified or that which is largely or for the most part specified, especially as these terms (i.e., "about," "substantial," or "substantially") are understood by a person with ordinary skill in the art. Any reference to a United States patent or other patent, and other printed publication set forth in this written description is incorporated in this written description in its entirety, including any reference cited in these references. All quantities expressed in percentages are percentages by weight, unless otherwise indicated.

The principles, various embodiments, and modes of operation of the present invention have been described in the foregoing written description. The invention, which is protected herein, i.e., the claimed invention, however, is to be construed as including variations or changes that may be made by those skilled in the art without departing from the spirit of the invention.

What is claimed is:

1. A process for producing a substantially stable dispersion comprising at least one hydrophobic plant sterol and an aqueous material comprising:
    mixing the at least one hydrophobic plant sterol with said aqueous material to form a first dispersion of particles of the at least one hydrophobic plant sterol and said aqueous material, wherein said aqueous material is chosen from at least one fruit juice concentrate and at least one fruit juice;
    heating the first dispersion of particles of the at least one hydrophobic plant sterol and said aqueous material to form a heated first dispersion;
    cooling the heated first dispersion to a temperature ranging from about 32° F. to about 212° F. for a period of time ranging from about 1 second to about 30 seconds; and
    homogenizing the heated first dispersion to obtain a second dispersion of particles of the at least one hydrophobic plant sterol and said aqueous material, wherein the particle size of the at least one hydrophobic plant sterol particles in said first dispersion is from about 0.1 microns to about 100 microns, or the particle size of the at least one hydrophobic plant sterol particles in said second dispersion is from about 0.1 microns to about 100 microns, or wherein the particle size of said hydrophobic plant sterol particles in both said first dispersion and said second dispersion is from about 0.1 microns to about 100 microns, with the proviso that the first and/or the second dispersion do not use emulsifiers, thickening agents and/or manufacturing aids to achieve the substantially stable dispersion of the at least one hydrophobic plant sterol in said aqueous material.

2. The process of claim 1 comprising heating the at least one hydrophobic plant sterol and the aqueous material to a temperature of from about 64° F. to about 148° F. for a period of time of from about 0.1 minute to about 120 minutes.

3. The process of claim 1 wherein said particle size of the at least one hydrophobic plant sterol in said first dispersion is from about 0.1 micron to about 50 microns or the particle size of the at least one hydrophobic plant sterol in said second dispersion is from about 0.1 micron to about 50 microns, or the particle size of the at least one hydrophobic plant sterol in both said first dispersion and said second dispersion is from about 0.1 micron to about 50 microns.

4. The process of claim 3 wherein said particle size of the at least one hydrophobic plant sterol in said first dispersion is from about 0.1 micron to about 30 microns or the particle size of the at least one hydrophobic plant sterol in said second dispersion is from about 0.1 micron to about 30 microns, or the particle size of the at least one hydrophobic plant sterol in both said first dispersion and said second dispersion is from about 0.1 micron to about 30 microns.

5. The process of claim 4 wherein the particle size of the at least one hydrophobic plant sterol in said first dispersion is from about 0.1 micron to about 10 microns or the particle size of the at least one hydrophobic plant sterol in said second dispersion is from about 0.1 micron to about 10 microns, or the particle size of the at least one hydrophobic plant sterol in both said first dispersion and said second dispersion is from about 0.1 micron to about 10 microns.

6. The process of claim 1 wherein the majority of the at least one hydrophobic plant sterol ranges in particle size from about 0.2 microns to about 10 microns.

7. The process of claim 6 wherein the majority of the at least one hydrophobic plant sterol ranges in particle size from about 0.2 microns to about 2.5 microns.

8. The process of claim 7 wherein the majority of the at least one hydrophobic plant sterol ranges in particle size from about 0.4 microns to about 1.5 microns.

9. The process of claim 8 wherein the majority of the at least one hydrophobic plant sterol ranges in particle size from about 0.3 microns to about 0.4 microns.

10. The process of claim 1 wherein the at least one hydrophobic plant sterol is selected from:
    sitosterol, campesterol, stigmasterol, spinosterol, taraxasterol, brassicasterol, desmosterol, chalinosterol, poriferasterol, clionasterol, and ergosterol.

11. The process of claim 1 wherein the at least one hydrophobic plant sterol is selected from hydrogenation products of plant sterols.

12. The process of claim 1 wherein the at least one hydrophobic plant sterol is selected from the hydrogenation products of sitosterol, campesterol, stigmasterol, spinosterol, taraxasterol, brassicasterol, desmosterol, chalinosterol, poriferasterol, clionasterol, and ergosterol.

13. The process of claim 1 wherein the at least one hydrophobic plant sterol is selected from:
    sitostanol, campestanol, stigmastanol, spinostanol, taraxastanol, brassicastanol, desmostanol, chalinostanol, poriferastanol, clionastanol, and ergostanol.

14. The process of claim 1 wherein said aqueous material includes solid materials either dissolved or dispersed therein, and wherein the solids content of said aqueous material is from about 200 to about 1000 grams per liter of said aqueous material.

15. The process of claim 14 wherein said aqueous material includes solid materials either dissolved or dispersed therein, and wherein the solids content of said aqueous material is from about 400 to about 900 grams per liter of said aqueous material.

16. The process of claim 15 wherein said aqueous material includes solid materials either dissolved or dispersed therein, and wherein the solids content of said aqueous material is from about 600 to about 800 grams per liter of said aqueous material.

17. The process of claim 1 wherein, in said first dispersion, the at least one hydrophobic plant sterol is present in an amount from about 1 to about 100 grams per liter of said aqueous material.

18. The process of claim 17 wherein, in said first dispersion, the at least one hydrophobic plant sterol is present in an amount from about 10 to about 60 grams per liter of said aqueous material.

19. The process of claim 18 wherein, in said first dispersion, the at least one hydrophobic plant sterol is present in an amount from about 20 to about 30 grams per liter of said aqueous material.

20. The process of claim 1 wherein the first dispersion of particles of the at least one hydrophobic plant sterol is heated to a temperature of from about 110° F. to about 212° F. for a period of time of from about 1 second to about 20 seconds to form the heated first dispersion.

21. The process of claim 20 wherein said heated first dispersion is cooled to a temperature ranging from about 72° F. to about 160° F. for a period of time of from about 1 second to about 12 seconds.

22. The process of claim 20 wherein said aqueous material comprises at least one citrus juice concentrate.

23. The process of claim 22 wherein water is added to said second dispersion of particles of the at least one hydrophobic plant sterol and the at least one citrus juice concentrate to obtain an aqueous beverage mixture.

24. The process of claim 23 wherein the aqueous beverage mixture has a concentration of about 11° Brix to about 13° Brix.

25. The process of claim 22 wherein the at least one citrus juice concentrate is orange juice concentrate.

26. A product produced by the process of claim 25.

27. A product produced by the process of claim 22 wherein the citrus juice is orange juice, and the viscosity of the substantially stable dispersion is from about 100 cps to about 30,000 cps.

28. The product of claim 27 wherein the viscosity of the substantially stable dispersion is from about 6,000 cps to about 18,000 cps.

29. The process of claim 1 wherein said homogenizing is carried out at a pressure of from about 100 psi to about 14,500 psi.

30. The process of claim 29 wherein said homogenizing is carried out at a pressure of from about 500 psi to about 10,000 psi.

31. The process of claim 30 wherein said homogenizing is carried out at a pressure of from about 1,000 psi to about 5,000 psi.

32. The process of claim 31 wherein said homogenizing is carried out at a pressure of from about 2,000 psi to about 5,000 psi.

33. The process of claim 21 wherein said homogenizing is carried out at a pressure of from about 2,000 psi to about 5,000 psi.

34. The process of claim 1 wherein said homogenizing is carried out in multiple stages, at different pressures and/or at different temperatures.

35. The process of claim 34 wherein said homogenizing is carried out at a pressure of from about 2000 psi to about 5000 psi followed by a second homogenizing at a pressure of from about 300 psi to about 1000 psi and at a temperature of from about 72° F. to about 160° F.

36. The process of claim 1, wherein water is added to said second dispersion of particles of the at least one hydrophobic plant sterol and the at least one fruit juice concentrate to obtain an aqueous beverage mixture.

37. The process of claim 36 wherein the aqueous beverage mixture has a concentration of about 11° Brix to about 13° Brix.

38. The process of claim 1 wherein the viscosity of the substantially stable dispersion is from about 100 cps to about 30,000 cps.

39. The process of claim 38 wherein the viscosity of the substantially stable dispersion is from about 5,000 cps to about 30,000 cps.

40. The process of claim 39 wherein the viscosity of the substantially stable dispersion is from about 6,000 cps to about 18,000 cps.

41. The process of claim 40 wherein the viscosity of the substantially stable dispersion is from about 8,000 cps to about 15,000 cps.

42. The process of claim 1 further comprising adding at least one vitamin either before, during, or after the production of the substantially stable dispersion.

43. The process of claim 42 wherein the at least one vitamin is chosen from at least one of water soluble vitamins and oil soluble vitamins.

44. A product produced by the process of claim 1.

45. The product of claim 44 wherein the viscosity of the substantially stable dispersion is from about 100 cps to about 30,000 cps.

46. The product of claim 45 wherein the viscosity of the substantially stable dispersion is from about 5,000 cps to about 30,000 cps.

47. The product of claim 46 wherein the viscosity of the substantially stable dispersion is from about 6,000 cps to about 18,000 cps.

48. The product of claim 47 wherein the viscosity of the substantially stable dispersion is from about 8,000 cps to about 15,000 ops.

49. A composition comprising a substantially stable dispersion of at least one hydrophobic plant sterol and an aqueous material wherein the at least one plant sterol is selected from plant sterols and plant stanols, where in order to substantially avoid a powdery taste in the substantially stable dispersion, the particle size of the at least one hydrophobic plant sterol particles is from about 0.1 micron to about 30 microns and the majority of the at least one hydrophobic plant sterol particles within this range will be from about 0.2 microns to about 10 microns and will substantially follow a bell curve distribution and wherein the dispersion of the at least one hydrophobic plant sterol and aqueous material is prepared by mixing the at least one hydrophobic plant sterol with the aqueous material to form a first dispersion of particles of the at least one hydrophobic plant sterol and the aqueous material wherein said aqueous material chosen from at least one fruit juice concentrate and at least one fruit juice; heating the first dispersion of particles of the at least one hydrophobic plant sterol and the aqueous material to form a heated first dispersion; cooling the heated first dispersion to a temperature ranging from about 32° F. to about 212° F. for a period of time ranging from about 1 second to about 30 seconds; and homogenizing the heated first dispersion to obtain a second dispersion of particles of the at least one hydrophobic plant sterol and the aqueous material, with the proviso that the first and/or the second dispersion do not use emulsifiers, thickening agents and/or manufacturing aids to achieve the substantially stable dispersion of the at least one hydrophobic plant sterol in said aqueous material.

50. The composition of claim 49 wherein the size of the majority of the at least one hydrophobic plant sterol particles are within the range of from about 0.2 microns to about 2.5 microns and substantially follow a bell curve distribution.

51. The composition of claim 50 wherein the size of the majority of the at least one hydrophobic plant sterol particles fall within the range of from about 0.3 microns to about 0.4 microns and substantially follow a bell curve distribution.

52. The composition of claim 49 wherein said hydrophobic plant sterol is selected from:
sitosterol, campesterol, stigmasterol, spinosterol, taraxasterol, brassicasterol, desmosterol, chalinosterol, poriferasterol, clionasterol, and ergosterol.

53. The composition of claim 49 wherein the at least one hydrophobic plant sterol is selected from the hydrogenation products of plant sterols.

54. The composition of claim 49 wherein the at least one hydrophobic plant sterol is selected from the hydrogenation products of sitosterol, campesterol, stigmasterol, spinosterol, taraxasterol, brassicasterol, desmosterol, chalinosterol, poriferasterol, clionasterol, and ergosterol.

55. The composition of claim 49 wherein the at least one hydrophobic plant sterol is selected from sitostanol, campestanol, stigmastanol, spinostanol, taraxastanol, brassicastanol, desmostanol, chalinostanol, poriferastanol, clionastanol, and ergostanol.

56. The composition of claim 49 wherein said aqueous material includes solid materials either dissolved or dispersed therein, and wherein the solids content of said aqueous material is from about 600 to about 800 grams per liter of said aqueous material.

57. The composition of claim 49 wherein, in said dispersion, the at least one hydrophobic plant sterol is present in an amount of from about 15 to about 30 grams per liter of liter of said aqueous material.

58. The composition of claim 49 wherein said aqueous material comprises at least one citrus juice concentrate.

59. The composition of claim 58 wherein the at least one citrus juice concentrate is orange juice concentrate.

60. The composition of claim 59 wherein the viscosity of the substantially stable dispersion is from about 100 cps to about 30,000 cps.

61. The composition of claim 60 wherein the viscosity of the substantially stable dispersion is from about 6,000 cps to about 18,000 cps.

62. The composition of claim 49 further comprising manufacturing aids selected from food grade emulsifiers, gums, starches, pectins, and pectin derivatives.

63. The composition of claim 49 further comprising water added to said fruit juice concentrate in an amount so that said concentrate is diluted to from about 11° Brix to about 13° Brix.

* * * * *

UNITED STATES PATENT AND TRADEMARK OFFICE
CERTIFICATE OF CORRECTION

| | | |
|---|---|---|
| PATENT NO. | : 7,335,389 B2 | Page 1 of 1 |
| APPLICATION NO. | : 10/458692 | |
| DATED | : February 26, 2008 | |
| INVENTOR(S) | : Erich P. Lerchenfeld et al. | |

It is certified that error appears in the above-identified patent and that said Letters Patent is hereby corrected as shown below:

*On the title page, item (57), line 7, "dispersion The" should read --dispersion.  The--.

*In claim 48, column 16, line 46, "ops." should read --cps--.

*In claim 49, column 16, line 63, "material chosen" should read --material is chosen--.

*In claim 57, column 18, lines 11-12, "liter of liter of said" should read --liter of said--.

Signed and Sealed this

First Day of July, 2008

JON W. DUDAS
*Director of the United States Patent and Trademark Office*